Patented Oct. 13, 1942

Plant Pat. 548

UNITED STATES PATENT OFFICE

548

SEEDLESS NAVEL ORANGE

Donald John Nicholson, Orlando, Fla.

No Drawing. Application September 12, 1941, Serial No. 410,628

1 Claim. (Cl. 47—62)

The new variety of navel orange tree which is described in this application, was first discovered by me about August 1934 in a small, isolated grove of mixed varieties of citrus, located on the shores of Lake Apopka, Lake County, Florida. In this out-of-the-way grove were found 25 trees of this very unusual and unique type of navel fruits, which immediately struck me as being different and distinct from that of any other type of navel oranges which I had ever seen before.

Several sticks of budwood were cut from branches producing the heaviest crops of finest-shaped fruits. From this budwood, buds were cut and used for top-working into limbs of old bearing orange trees and in budding on young orange seedlings, which resulted in the reproduction of the identical type fruits found on the parent tree.

To determine whether or not soil conditions or locations were responsible for the remarkable smooth, satin-like texture of rind of these fruits which were most uniform in this respect, plantings and top-working were done 35 miles away upon entirely different type of soil and environments, and upon fruiting were found to remain constant and like fruits produced on the parent tree.

The trees of this new variety of navel orange found in this original grove were huge budded trees showing exceptional vigor and absence of disease. They were of far greater size than any budded Bahia or Washington type navel orange known to me, some of the trees attaining heights of 25 or more feet, with stout trunks and branches; tops well-headed and dense of foliage. I should judge the age of these navel trees to be at least 35 years and possibly older.

Nothing seems to be known as to their origin and the variety is not found in any other grove so far as I can learn.

The fruits of this variety of navel were strikingly beautiful, fruits being of large size, deep orange or reddish color, with very smooth, satin-like glossy rind. Trees heavily laden with fruits. Later and continued observations showed the variety to be a consistent and heavy producer, frequently blooming profusely before January 15, while still carrying a heavy crop of matured fruits. While the fruits were found to be ripe and sweet and of good flavor about October 5, of each season, they were not well-filled with juice and were of a decided ricey appearance; however, this condition disappeared as the season advanced when the fruits always became heavy and juicy in November and December. In spite of their smooth rinds, they were tough and leathery-skinned, keeping for long periods in good condition.

The variety is remarkably seedless; 1800 fruits from two trees personally examined in a single day, contained but 35 seed in the entire lot among these normal-bloom fruits. Oddly enough, during another season I found a box and a half of much-delayed or so-called "June-bloom" fruits. These were examined for seeds and invariably each fruit contained from two to four or five seeds. A few normal-bloom fruits found at same time contained no seed.

Particularly noteworthy is the fact that initial crops on progeny buds, produce fruits with extremely smooth skins which are far smoother of texture than any fruits of the Bahia or Washington type navels on old trees.

Detailed description follows:

*Tree*

Large—vigorous—symmetrical and dense-headed—consistently heavy producer.

Trunk large, stocky.

Branches strong and spreading with numerous fruiting twigs.

Leaves medium thick, large, gradually pointed, dark green, glossy petioles medium length, narrow.

Flowers normally produced in January; profuse, setting fruit on inside as well as outside twigs and branches.

Thornless: Progeny buds thornless, however, some of the progeny buds are found producing thorns.

*Fruit*

Form rounded in majority of specimens, however, considerable variation exists, some being slightly oblate, oval, oblong, or distinctively top-shaped, some tapering gradually towards apex, others with flat apex, navel flush with opening; a few found with protruding navels (just occasional fruits); size large, ranging from 96's to 200's and averaging size 150 (basis Florida standard packed box); color deep orange or reddish tinge in fully matured specimens; base flat, sometimes rounded, smooth shoulders, rarely slightly creased; calyx small; stem small; apex navel-marked, umbilicus either concealed or exposed either fleshy and large extending inside 1½ inches or small and restricted; oil cells small, flush with surface or very slightly elevated; sections varying from 9 to 13, usually 10 or 11, sometimes irregular; flesh tender frequently parting in chunks when being eaten, yellowish; juice somewhat lacking during earliest maturity period, however, becoming quite heavy and juicy later, abundant when prime, acidity and sweetness well blended; flavor honey-like, delicious and pleasing; quality good; seeds none in greater part of crops, only an occasional fruit found with one or more seeds; plump or round as a marble, others flat and lima bean-shaped.

Season October to January and later according to weather.

I claim:

The new variety of navel orange herein disclosed, characterized by consistent and persistent production of very smooth, satin-like, glossy, tough-rinded, early-maturing fruit, and the habit of very slow and gradual filling of its juice cells after the early maturity.

DONALD JOHN NICHOLSON.